(12) United States Patent
Borody et al.

(10) Patent No.: US 10,434,114 B2
(45) Date of Patent: *Oct. 8, 2019

(54) METHODS OF TREATING A BACTERIAL INFECTION USING A FIXED-DOSE PHARMACEUTICAL COMPOSITION COMPRISING THREE ANTIBIOTICS

(71) Applicant: RedHill Biopharma Ltd., Tel-Aviv (IL)

(72) Inventors: Thomas Julius Borody, Five Dock (AU); Patrick Gosselin, Laval (CA)

(73) Assignee: RedHill Biopharma Ltd., Tel-Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/173,530

(22) Filed: Oct. 29, 2018

(65) Prior Publication Data

US 2019/0060343 A1 Feb. 28, 2019

Related U.S. Application Data

(63) Continuation of application No. 15/860,298, filed on Jan. 2, 2018, now Pat. No. 10,143,702, which is a continuation of application No. 15/585,879, filed on May 3, 2017, now Pat. No. 10,105,379, which is a continuation of application No. 15/131,533, filed on Apr. 18, 2016, now abandoned, which is a continuation of application No. 14/271,814, filed on May 7, 2014, now Pat. No. 9,314,477, which is a continuation of application No. 13/722,395, filed on Dec. 20, 2012, now Pat. No. 9,072,763, which is a continuation of application No. 12/918,310, filed as application No. PCT/AU2009/000129 on Feb. 5, 2009, now Pat. No. 8,343,511.

(60) Provisional application No. 61/065,144, filed on Feb. 8, 2008.

(51) Int. Cl.
| | |
|---|---|
| A61K 31/7048 | (2006.01) |
| A61K 31/395 | (2006.01) |
| A61K 31/498 | (2006.01) |
| A61K 31/44 | (2006.01) |
| A61K 31/438 | (2006.01) |
| A61K 31/435 | (2006.01) |
| A61K 9/00 | (2006.01) |
| A61K 47/10 | (2017.01) |
| A61K 9/48 | (2006.01) |

(52) U.S. Cl.
CPC ........ *A61K 31/7048* (2013.01); *A61K 9/0053* (2013.01); *A61K 9/48* (2013.01); *A61K 31/395* (2013.01); *A61K 31/435* (2013.01); *A61K 31/438* (2013.01); *A61K 31/44* (2013.01); *A61K 31/498* (2013.01); *A61K 47/10* (2013.01)

(58) Field of Classification Search
CPC .............. A61K 2300/00; A61K 31/395; A61K 31/498; A61K 31/7048; A61K 31/435; A61K 31/438; A61K 31/44; A61K 9/48; A61K 9/0053
See application file for complete search history.

*Primary Examiner* — Savitha M Rao
(74) *Attorney, Agent, or Firm* — Greenberg Traurig, LLP

(57) ABSTRACT

Oral administration of a solid dosage form of the present invention comprising an effective amount of rifabutin, an effective amount of clarithromycin, an effective amount of clofazimine, and an effective amount of an absorption enhancer, is used to treat a subject suffering from, or susceptible to, *Mycobacterium avium* subspecies *paratuberculosis* infection. In an embodiment, the solid dosage form is sufficiently designed to result in a reduction in the increased metabolism of clarithromycin caused by rifabutin. In an embodiment, the solid dosage form is sufficiently designed to result in a reduction in the metabolism of rifabutin caused by clarithromycin. In an embodiment, the solid dosage form is sufficiently designed to result in a reduction in risk of a subject developing leucopenia or uveitis as a result of rifabutin.

11 Claims, 5 Drawing Sheets

METHODS OF TREATING A BACTERIAL INFECTION USING A FIXED-DOSE PHARMACEUTICAL COMPOSITION COMPRISING THREE ANTIBIOTICS

RELATED APPLICATIONS

This application is a continuation of U.S. patent application Ser. No. 15/860,298, filed Jan. 2, 2018, which is a continuation of U.S. patent application Ser. No. 15/585,879, filed May 3, 2017, now U.S. Pat. No. 10,105,379, which is a continuation of U.S. patent application Ser. No. 15/131,533, filed Mar. 18, 2016, which is a continuation of U.S. patent application Ser. No. 14/271,814, filed May 7, 2014, now U.S. Pat. No. 9,314,477, which is a continuation of U.S. patent application Ser. No. 13/722,395, filed Dec. 20, 2012, now U.S. Pat. No. 9,072,763 which is a continuation of U.S. patent application Ser. No. 12/918,310, filed Nov. 29, 2010, now U.S. Pat. No. 8,343,511, which is a National Stage Entry of PCT/AU09/00129, filed Feb. 5, 2009, which claims the benefit of and priority to U.S. Provisional Application Ser. No. 61/065,144, filed Feb. 8, 2008, the entirety of these applications are hereby incorporated herein by reference.

BACKGROUND

Inflammatory bowel disease (IBD) is a disorder of unknown etiology characterized typically by diarrhea, cramping, abdominal pains, weight loss and rectal bleeding, tiredness, anemia, fistulae, perforations, obstruction of the bowel and frequent need for surgical intervention. It encompasses a number of disorders including Crohn's disease, ulcerative colitis, indeterminate colitis, microscopic colitis and collagenous colitis. Such disorders may at times begin clinically with a more benign or milder presentation, resembling Irritable Bowel Syndrome (IBS) which can subsequently progress to increasing inflammation accompanying the IBS and may ultimately develop full-blown IBD. The precise causes of IBD and IBS remain unknown. However, there has been a rapidly growing evidence base that *Mycobacterium avium* subspecies *paratuberculosis* (MAP), and perhaps its various strains and sub-strains, are involved in a variety of different diseases and may play an infective role in a significant proportion of patients with Crohn's disease and may co-exist in other inflammatory bowel disorders listed above.

Accordingly, there was a need for an effective treatment of MAP-infected IBD, and in particular Crohn's disease. U.S. Pat. No. 6,277,863 to Borody ("Borody") describes treatment of IBD using rifabutin in combination with the macrolide clarithromycin and clofazimine. These were prescribed to be ingested simultaneously but as separate tablets and capsules. It was found that taking the capsules and tablets simultaneously caused unwanted interactions of the medications including a marked elevation in the serum of rifabutin at the expense of suppressing the clarithromycin, whose serum concentrations found later in pharmacokinetic studies, came close to suboptimal even at the recommended oral drug doses, threatening resistance development (Hafner, R., et al., Antimicrobial Agents and Chemotherapy, March 1998, Vol. 42, No. 3, pages 631-639), Conversely, this produced a situation where some patients had blood drug levels which were bordering on adverse effect ranges, e.g., possibly close to causing leucopenia or uveitis. In addition, clofazimine levels with separate drugs were slow to reach equilibrium.

Considering the above described unwanted interactions and the undesired results of Borody, an improved formulation was desired to address these shortcomings.

SUMMARY

In one aspect, the present disclosure provides a pharmaceutical composition comprising rifabutin, clarithromycin, clofazimine, and a pharmaceutically acceptable carrier, wherein the amount of clofazimine is 10-15% w/w relative to the amount of clarithromycin and 20-25% w/w relative to the amount of rifabutin.

In one embodiment, the present disclosure provides a method of increasing the reduced metabolism of rifabutin caused by clarithromycin in a patient, comprising co-administering clofazimine with rifabutin and clarithromycin to the patient, wherein the amount of clofazimine is 6-18% w/w relative to the amount of clarithromycin.

Also provided is a method of reducing the increased metabolism of clarithromycin caused by rifabutin in a patient, comprising co-administering clofazimine with rifabutin and clarithromycin to the patient, wherein the amount of clofazimine is 6-18% w/w relative to the amount of clarithromycin.

The present disclosure, in some embodiments, provides a method of treating a patient suffering from or susceptible to a *Mycobacterium paratuberculosis* infection, comprising co-administering to the patient in a single dosage form rifabutin, clarithromycin, and clofazimine in a 9±0.5: 19±0.5:2±0.5 w/w/w ratio.

Also contemplated is a method of inhibiting occurrence of a *Mycobacterium paratuberculosis* infection in a patient, comprising simultaneously co-administering to the patient in need thereof (i) 225 mg±2 mg rifabutin, (ii) 475 mg±2 mg clarithromycin, and (iii) 50 mg±1 mg clofazimine once each day.

BRIEF DESCRIPTION OF THE DRAWINGS

The following figures depict illustrative aspects of present compositions and methods and not intended to be limiting in any way.

DETAILED DESCRIPTION

1. Compositions

Figure 1A:
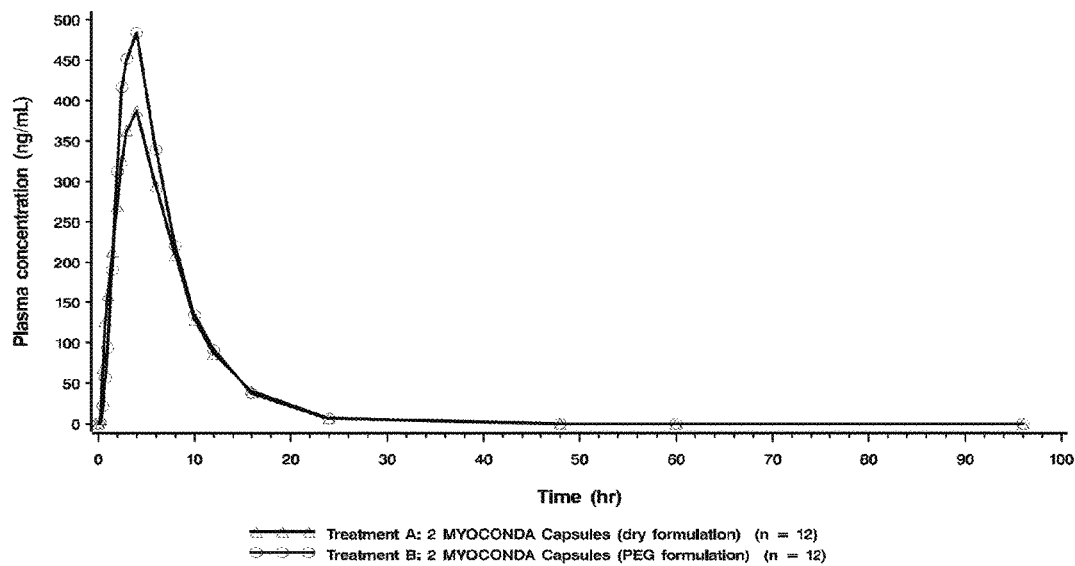
FIGS. 1*a-b* depict mean clarithromycin plasma concentration-time profiles in linear and semi-logarithmic plots, respectively.

The present description provides compositions comprising rifabutin, clarithromycin, and clofazimine and methods of using same. The rifabutin, clarithromycin, and clofazimine of the compositions are provided in ratios that yield improved pharmacokinetic properties. The present compositions reduce potentially deleterious elevations of rifabutin serum concentration that resulted from administration of earlier known formulations. In contrast to earlier known formulations, the present compositions further provide the advantage of maintaining patient blood drug levels well below adverse effect ranges, e.g., below ranges implicating leucopenia or uveitis. Moreover, the subject compositions also maintain higher levels of serum concentrations of clarithromycin as compared to earlier formulations, thereby inhibiting resistance development. Furthermore, the present compositions allow reaching minimum effective patient clofazimine serum levels faster than with previous formulations.

In one embodiment, present compositions comprise rifabutin, clarithromycin, clofazimine, and a pharmaceutically acceptable carrier, wherein the amount of clofazimine is 5-18% w/w relative to the amount of clarithromycin (such as, 7-16%, 9-14%, 9-12%, 10-15%, or 0-11% w/w) and 10-25% w/w relative to the amount of rifabutin (such as, 12-25%, 12-23%, 15-25%, 15-23%, 18-25%, 18-23%, 20-25%, 20-23%, or 21-23%).

In further embodiments, the present compositions comprise rifabutin, clarithromycin, and clofazimine in about a 9:19:2 w/w/w ratio, wherein each of the variables are free to vary ±2, 1, 0.5, or 0.25 (e.g., 9±0.5:19±5:2±0.5). For example in some instances, the present compositions comprise 90 mg rifabutin (±30, 20, 10, 5, 2, or 1 mg), 190 mg clarithromycin (±60, 40, 20, 10, 5, 2, or 1 mg), and 20 mg clofazimine (±10, 7, 5, 2, or 1 mg). In another instance, the present compositions comprise 45 mg rifabutin (±15, 10, 7, 5, 2, or 1 mg), 95 mg clarithromycin (±30, 20, 10, 5, 2, or 1 mg), and 10 mg clofazimine (±6, 5, 2, or 1 mg).

In some instances the present compositions further comprise an absorption enhancer that may improve bioavailability of one or more of the active ingredients. The amount of absorption enhancer may between 300-700% w/w relative to the amount of clofazimine including 400-600% or 450-550% or 475-525%. In certain embodiments, the absorption enhancer is polyethylene glycol (PEG), for example, polyethylene glycol having an average molecular weight of between 200-20,000 including between 1000-15000 or 5000-12000 or 7000-9000 or 7500-8500, for example PEG 8000).

The present compositions may further include one or more additional excipients, such as Microcrystalline cellulose (MCC)TABULOSE® SC 200), Mg Stearate, Sodium Lauryl Sulfate (SLS) EMAL® 10Pwd HD, a polysorbate (such as, polysorbate 80), or a combination thereof, including all of these. In some instances, the present compositions include both polyethylene glycol and a polysorbate, such as polysorbate 80, wherein the amount of polysorbate is 30-120% w/w relative to the amount of clofazimine (such as 50-100%, 50-85%, or 60-75%). Additional excipients contemplated for use with the present compositions are described further below.

The present compositions may further include one or more ionic or non-ionic surfactants. In particular, the present compositions may comprise sodium lauryl sulfate.

In one embodiment, the present compositions are provided in a single dosage form, for example a tablet, capsule, caplet or lozenge, etc. Additional contemplated dosage forms are described further below.

2. Methods of Treatment

The present compositions are useful for treating a patient suffering from or susceptible to a *Mycobacterium paratuberculosis* (MAP) infection. In some instances, such treatments include the treatment of inflammatory bowel disease (IBD), such as Crohn's disease, ulcerative colitis, indeterminate colitis, microscopic colitis and collagenous colitis, in addition to sarcoidosis. In preferred embodiments, the present methods are useful for the treatment of Crohn's disease or colitis.

Hence, in one embodiment the present methods include a method of treating a patient suffering from or susceptible to a *Mycobacterium paratuberculosis* infection, comprising co-administering to the patient in a single dosage form rifabutin, clarithromycin, and clofazimine in a 8-10:18-20:1-2.5 w/w/w ratio (for example, a 8.5-9.5:18.5-19.5:1.5-2.5 w/w/w ratio or a 9:19:2 ratio, wherein each variable is free to vary ±0.5 or 0.25). In another embodiment, the present method may include a composition comprising a single dosage form comprising 90 mg rifabutin (±30, 20, 10, 5, 2, or 1 mg), 190 mg clarithromycin (±60, 40, 20, 10, 5, 2, or 1 mg), and 20 mg clofazimine (±10, 7, 5, 2, or 1 mg). In another embodiment, the present method may include a composition comprising 45 mg rifabutin (±15, 10, 7, 5, 2, or 1 mg), 95 mg clarithromycin (±30, 20, 10, 5, 2, or 1 mg), and 10 mg clofazimine (±6, 5, 2, or 1 mg).

In some instances, the rifabutin, clarithromycin, and clofazimine are co-administered once each day for a first period of treatment (for example, 1-3 weeks, including 1 week, 2 weeks or three weeks) in the following amounts: (i) 80-100 mg rifabutin (such as, 85-95 mg or 90 mg±1.5 mg), (ii) 180-200 mg clarithromycin (such as, 185-195 mg or 190 mg±2 mg), and (iii) 15-25 mg clofazimine (such as 17-23 mg or 20±1 mg). The method may further include the step of linearly increasing the amounts of the rifabutin, clarithromycin, and clofazimine while maintaining a 8-10:18-20:1-2.5 w/w/w ratio (for example, a 8.5-9.5:18.5-19.5:1.5-2.5 w/w/w ratio or a 9:19:2 ratio, wherein each variable is free to vary ±0.5 or 0.25 ratio) for a second period of treatment (for example, from 4-10 weeks). In an embodiment, the linearly increasing amounts of the rifabutin, clarithromycin, and clofazimine do not exceed maximum amounts of (i) 420-480 mg rifabutin (such as, 440-460 mg or 450 mg), 920-980 mg clarithromycin (such as, 940-960 mg or 950 mg), and (iii) 80-120 mg clofazimine (such as, 90-110 mg or 100 mg) during the second period of treatment. In certain instances, the linearly increasing amounts of rifabutin, clarithromycin, and clofazimine comprise:

a) (i) 160-200 mg rifabutin (such as, 170-190 mg or 180 mg±2 mg), (ii) 360-400 mg clarithromycin (such as, 370-390 mg or 380 mg±2 mg), and (iii) 30-50 mg clofazimine (such as, 35-45 mg or 40 mg±1 mg) once each day for two weeks;

b) (i) 250-290 mg rifabutin (such as, 260-280 mg or 270 mg±2 mg), (ii) 550-590 mg clarithromycin (such as, 560-580 mg or 570±2 mg), and (iii) 50-70 mg clofazimine (such as, 55-65 mg or 60 mg±1.5 mg) once each day for two weeks;

c) (i) 340-380 mg rifabutin (such as, 350-370 mg or 360 mg±2 mg), (ii) 740-780 mg clarithromycin (such as 750-770 mg or 760 mg±2 mg), and (iii) 60-100 mg clofazimine (such as, 70-90 mg or 80 mg±1.5 mg) once each day for two weeks; and d) (i) 420-480 mg rifabutin (such as, 440-460 mg or 450 mg±2 mg), (ii) 920-980 mg clarithromycin (such as, 940-960 mg or 950 mg±2 mg), and (iii) 80-120 mg clofazimine (such as, 90-110 mg or 100 mg±1.5 mg) once each day for a week.

In certain embodiments, the method further includes, following step d) above, the step of simultaneously co-administering (i) 420-480 mg rifabutin (such as, 440-460 mg or 450 mg±2 mg), (ii) 920-980 mg clarithromycin (such as, 940-960 mg or 950 mg±2 mg), and (iii) 80-120 mg clofazimine (such as, 90-110 mg or 100 mg±1.5 mg) once each day for a third period of treatment. In some embodiments, the third period of treatment is 1, 2, 4, 6, 8, 12 weeks; 3, 6, or 12 months or longer. In one embodiment the third period of treatment continues until the MAP infection has been treated, for example, to the point of eradication, reduction, or at least to the point of halting the progression of the infection.

In some instances, the method further includes, after the MAP infection has been treated, the step of simultaneously co-administering to the patient (i) 210-240 mg rifabutin (such as, 220-230 mg or 225 mg±2 mg), (ii) 460-490 mg clarithromycin (such as, 470-480 mg or 475 mg±2 mg), and (iii) 40-60 mg clofazimine (such as, 45-55 mg or 50 mg±1 mg) once each day, for example, to inhibit recurrence or prevent recurrence of MAP infection. In some instances, the patient was previously treated with a combination of rifabutin, clarithromycin, and clofazimine. Also contemplated is a method of inhibiting occurrence of a *Mycobacterium paratuberculosis* infection in a patient, comprising simultaneously co-administering to the patient in need thereof (i) 210-240 mg rifabutin (such as, 220-230 mg or 225 mg±2 mg), (ii) 460-490 mg clarithromycin (such as, 470-480 mg or 475 mg±2 mg), and (iii) 40-60 mg clofazimine (such as, 45-55 mg or 50 mg±1 mg) once each day.

The present methods further contemplate a method of increasing the reduced metabolism of rifabutin caused by clarithromycin in a patient; comprising co-administering clofazimine with rifabutin and clarithromycin to the patient, wherein the amount of clofazimine is 5-18% w/w relative to the amount of clarithromycin, for example, 6-18%, 7-16%, 9-14%, 9-12%, 10-15%, or 10-11% w/w.

In another embodiment, the present methods further include a method of reducing the increased metabolism of clarithromycin caused by rifabutin in a patient, comprising co-administering clofazimine with rifabutin and clarithromycin to the patient, wherein the amount of clofazimine is 5-18% w/w relative to the amount of clarithromycin, for example, 6-18%, 7-16%, 9-14%, 9-12%, 10-15%, or 10-11% w/w.

The present methods further contemplate a method of increasing the reduced metabolism of rifabutin caused by clarithromycin in a patient, comprising co-administering clofazimine with rifabutin and clarithromycin to the patient, wherein the amount of clofazimine is 10-25% w/w relative to the amount of rifabutin, for example, 12-25%, 12-23%, 15-25%, 15-23%, 18-25%, 18-23%, 20-25%, 20-23%, or 21-23% w/w.

In another embodiment, the present methods further include a method of reducing the increased metabolism of clarithromycin caused by rifabutin in a patient, comprising co-administering clofazimine with rifabutin and clarithromycin to the patient, wherein the amount of clofazimine is 10-25% w/w relative to the amount of rifabutin, for example, 12-25%, 12-23%, 15-25%, 15-23%, 18-25%, 18-23%, 20-25%, 20-23%, or 21-23% w/w.

In certain instances, the increase in rifabutin metabolism in the above methods is assessed by measuring a first $C_{max}$ of rifabutin or 25-O-desacetyl rifabutin in the patient's serum following administration of clofazimine and comparing the first $C_{max}$ to a second $C_{max}$ of rifabutin or 25-O-desacetyl rifabutin. The second $C_{max}$, of rifabutin or 25-O-desacetyl rifabutin may correspond to a reference value, for example, an average or mean value obtained from the literature, from one or more other patients with similar physical profiles (age, health, metabolism, and/or disease profile, etc.) or from the same patient at an earlier time. For instance, in some embodiments, the second $C_{max}$ of rifabutin or 25-O-desacetyl rifabutin is measured in a second patient's serum, wherein the second patient has been co-administered rifabutin and clarithromycin without co-administration of clofazimine. In another embodiment, the second $C_{max}$ of rifabutin or 25-O-desacetyl rifabutin was previously measured in the same patient's serum, wherein the same patient had been co-administered rifabutin and clarithromycin without co-administration of clofazimine.

In one embodiment, the first $C_{max}$ of rifabutin is decreased as compared to the second $C_{max}$ of rifabutin by at least 5%, 10%, 20%, 30, or 40%. In another embodiment, the first $C_{max}$ of 25-O-desacetyl rifabutin is decreased as compared to the second $C_{max}$ of 25-O-desacetyl rifabutin by at least 5%, 10%, 20%, 30, or 40%.

In some instances, the increase in rifabutin metabolism in the above methods is assessed by measuring a first $AUC_{0-24}$ of 25-O-desacetyl rifabutin in the patient's serum following co-administration of clofazimine and comparing the first AUC to a second $AUC_{0-24}$ of 25-O-desacetyl rifabutin. The second $AUC_{0-24}$ of 25-O-desacetyl rifabutin may correspond to a reference value, for example, an average or mean value obtained from the literature, from one or more other patients with similar physical profiles (age, health, metabolism, and/or disease profile, etc.) or from the same patient at an earlier time. For example, in certain instances, the second $AUC_{0-24}$ of 25-O-desacetyl rifabutin is measured in a second patient's serum, wherein the second patient has been co-administered rifabutin and clarithromycin without co-administration of clofazimine. In another embodiment, the second $AUC_{0-24}$ of 25-O-desacetyl rifabutin was previously measured in the same patient's serum, wherein the same patient had been co-administered rifabutin and clarithromycin without co-administration of clofazimine.

In one embodiment, the first $AUC_{0-24}$ is decreased as compared to the second $AUC_{0-24}$ by at least 5%, 10%, 20%, 30, or 40%.

For the compositions employed in the present methods, in some instances, at least two of the rifabutin, the clarithromycin, and the clofazimine are co-formulated into a single dosage form. For example, in some instances, each of the rifabutin, the clarithromycin, and the clofazimine are co-formulated into a single dosage form.

Any of the above-mentioned compositions are contemplated for use with the present methods. For example, in some instances the present methods contemplate use of compositions comprising an absorption enhancer that may improve bioavailability of one or more of the active ingredients. The amount of absorption enhancer may between 300-700% w/w relative to the amount of clofazimine (such as, 400-600%, 450-550%, or 475-525%). In certain embodiments, the absorption enhancer is polyethylene glycol, for example, polyethylene glycol having an average molecular weight of between 200-20,000 (such as, between 1000-15000, 5000-12000, 7000-9000, or 7500-8500, for example PEG 8000).

3. Methods Including Immunization with Mycobacterial Extract or Product

The present methods further contemplate a method for the treatment of inflammatory bowel disease comprising administering to a patient in need of such treatment effective amounts of rifabutin, clarithromycin, and clofazimine, in ratios, dosages, and/or dosage forms as described herein, and immunizing the patient with an immunizing amount of a mycobacterial extract or product. For example, a patient previously not treated or on current anti-inflammatory therapies may be treated by immunization with a mycobacterial extract or product (living or dead, or its extracted wall and DNA components) as an immunizing agent to stimulate leucocytes in the immunized patient. Such immunizing agents may be extracts or products from known, non-pathogenic mycobacteria such as *M. vaccae* of *M. phlei*. As used herein, the expression "mycobacterial extract or product" refers to whole-killed mycobacteria or mycobacterial extract, with or without adjuvants. An example of a suitable mycobacterial product or extract is Regressin, available from Bioniche of London, Ontario, Canada.

The mycobacterial product may be used to recurrently immunize the patient using the product as an immuno-stimulant. The mycobacterial product can be administered via any of several routes, such as oral, intravenous, intramuscular, or subcutaneous. Such immunizations can reduce or even rid the patient of the MAP infection and have the ability to inhibit or cure the disease or place the patient into a prolonged remission.

Administration of the mycobacterial product or extract is typically from weekly to monthly, but may be more or less frequent. An appropriate treatment regime may be arrived at readily by a medical practitioner in any particular case, given the teaching herein. The mycobacterial product or extract may be administered before, after, or simultaneous to administration of rifabutin, clarithromycin, and clofazimine.

Doses of the mycobacterial extract can be given in any frequency ranging from 25-500 µg, for example, 50-500 µg. In certain embodiments; adequate immuno-stimulation can be maintained by weekly to monthly, typically weekly or monthly, regimens.

In another embodiment, therapy with *Mycobacterium phlei* extract (e.g., Regressin) includes a weekly immunization program, increasing the dosage by 20-80 µg, for example, 40-60 µg or 50 µg, of the extract every week until the patient develops fever, rigors, and nausea.

The dose is then dropped by 20-80 µg, for example, 40-60 µg or 50 µg, to the lower level and the patient continues maintenance immunization on a monthly basis. The treatment can last from 4-8 weeks, such as 6 weeks, up to a monthly immunization program of 1-2 years or more.

In another form of therapy standard anti-inflammatory therapy can be combined with recurrent Regressin immunization.

Dosages of rifabutin, clarithromycin, and clofazimine used in conjunction with mycobacterial extract correspond to those described above. All combinations of the dosages and treatment schedules for rifabutin, clarithromycin, and clofazimine and mycobacterial extract described herein are contemplated.

4. Additional Agents

The present methods further contemplate combined use with one or more additional agents, such as anti-TB agents, such as salazopyrin, olsalazine or mesalazine, as well as other less known aminosalicylic acids. The 4-aminosalicylic acids or 5-aminosalicylic acids can be combined with rifabutin, clarithromycin, and clofazimine. Dosages of these additional agents are generally known. For example the typical dosage range for salazopyrin is in the range of from 500 mg to 4 g per day, and for olsalazine or mesalazine from 0.500 mg to 3 g per day.

Hence, the present methods may further include one or more agents effective against tuberculosis.

Such additional agents may be administered before, after, or simultaneous to administration of rifabutin, clarithromycin, and clofazimine. Furthermore, such agents may be administered as part of the same dosage form (e.g., tablet, capsule, caplet, etc.) or in a different dosage form as that including the rifabutin, clarithromycin, and clofazimine.

5. Dosage Forms

The present compositions may be available in the form of a tablet containing at least one of rifabutin, clarithromycin, and clofazimine in a powdered form. In some instances two or all of rifabutin, clarithromycin, and clofazimine are in a powdered form. Alternatively, present compositions may be in the form of a tablet capsule containing at least one of rifabutin, clarithromycin, and clofazimine in a microencapsulated form. In some instances, two or all of rifabutin, clarithromycin, and clofazimine are in a microencapsulated form. As another possibility, present compositions may be in the form of a tablet capsule containing at least one of rifabutin, clarithromycin, and clofazimine in a powdered form, and the remaining agents present in a microencapsulated form. As a further possibility, present compositions may be in the form of a tablet capsule containing one or more of rifabutin, clarithromycin, and clofazimine present in a microgranulated form. In additional possibilities, present compositions may be in the form of a tablet containing one or more of rifabutin, clarithromycin, and clofazimine within a capsule, a capsule containing one or more of rifabutin, clarithromycin, and clofazimine within a tablet, a capsule containing one or more of rifabutin, clarithromycin, and clofazimine within an outer capsule containing the other agents, or any combination of the above.

In a further embodiment, the present compositions comprise an inner capsule containing rifabutin, within an outer capsule containing clarithromycin and clofazimine, wherein clarithromycin and clofazimine may be present in powdered, microencapsulated, or microgranulated forms.

The present methods may be carried out by administration of one or more tablets/capsules containing rifabutin, clarithromycin, and clofazimine as described above, or through the administration of each of these separately. In preferred embodiments, rifabutin, clarithromycin, and clofazimine are administered simultaneously in one dose.

The present compositions may be prepared by means known in the art for the preparation of pharmaceutical compositions including blending, grinding, homogenizing, suspending, dissolving, emulsifying, dispersing, and, where appropriate, mixing of rifabutin, clarithromycin, and clofazimine together with selected excipients, diluents, carriers and adjuvants.

For oral administration, the present compositions may be in the form of tablets, lozenges, pills, troches, capsules, elixirs, powders, including lyophilized powders, solutions, granules, suspensions, emulsions, syrups and tinctures. Slow-release, or delayed-release, forms may also be prepared, for example in the form of coated particles, multilayer tablets or microgranules.

Solid forms for oral administration may contain pharmaceutically acceptable binders, sweeteners, disintegrating agents, diluents, flavorings, coating agents, preservatives, lubricants, and/or time delay agents. Suitable binders include gum acacia, gelatin, corn starch, gum tragacanth, sodium alginate, carboxymethylcellulose or polyethylene glycol (PEG). Suitable sweeteners include sucrose, lactose, glucose, aspartame or saccharine. Suitable disintegrating agents include corn starch, methylcellulose, polyvinylpyrrolidone, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavoring agents include peppermint oil, oil of wintergreen, cherry, orange, or raspberry flavoring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils, such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides, or mixtures thereof.

Suspensions for oral administration may further include dispersing agents and/or suspending agents. Suitable suspending agents include sodium carboxymethylcellulose, methylcellulose, hydroxypropylmethyl-cellulose, poly-vinyl-pyrrolidone, sodium alginate or ceryl alcohol. Suitable dispersing agents include lecithin, polyoxyethylene esters of fatty acids such as stearic acid, polyoxyethylene sorbitol mono- or di-oleate, -stearate or laurate, polyoxyethylene sorbitan mono- or -dioleate, -stearate or -laurate, and the like.

Emulsions for oral administration may further include one or more emulsifying agents. Suitable emulsifying agents include dispersing agents as exemplified above or natural gums such as gum acacia or gum tragacanth.

Variations, modifications, and other implementations of what is described herein will occur to those of ordinary skill without departing from the spirit and the scope of the present disclosure. Accordingly, these are not to be limited only to the preceding illustrative description.

For additional illustrative features that may be used with the present compositions and methods, including the embodiments described here, refer to the documents listed herein, which are incorporated by reference in their entirety. All operative combinations between the above described illustrative embodiments and those features described in documents and references cited herein are considered to be potentially patentable embodiments.

Exemplification

With aspects of the present compositions and methods now being generally described, these will be more readily understood by reference to the following examples, which are included merely for purposes of illustration of certain features and embodiments of the present compositions and methods invention and are not intended to be limiting.

1. Bioavailability Study

The objectives of this study were to 1) determine and compare the rate and extent of absorption and 2) to assess the safety and tolerability of 2 test formulations of a combination product of clarithromycin, rifabutin and clofazimine (herein after "triple combination").

This study followed a randomized, open-label, single-dose, 1-way 2-arm parallel design in 24 normal, healthy, non-smoking male and female subjects. All subjects completed the study, and their data were used for pharmacokinetic and statistical analyses.

Subjects were admitted to the clinic the day before dosing, and remained until the 24.00 hour post-dose blood draw, at which time they were allowed to leave the clinic and after which they were required to return for subsequent blood draws. Following a high fat meal, subjects received 2 triple combination capsules (dry formulation) or 2 triple combination capsules (PEG formulation) on Day 1 of the study period.

During the study, 19 blood samples were collected from each subject, for pharmacokinetic and statistical analyses. Over the course of the entire study, approximately 236.5 mL of blood was collected from male subjects and approximately 241.5 mL of blood was collected from female subjects. These volumes include all required samples, as described further below.

The randomization scheme was computer-generated and subjects were assigned a 15 treatment sequence before Period I dosing.

This was an open-label study; however, the bioanalytical group was blinded to the randomization scheme. This scheme was made available for statistical and reporting purposes only after the completion of the bioanalytical portion of the study.

Water was provided ad libitum until 1.0 hour pre-dose and after 1.0 hour post-dose. With the exception of the whole milk provided to all subjects during the high fat content meal, the only fluid intake allowed during this time was 240 mL of ambient temperature dosing water.

Following an overnight fast of at least 10 hours, subjects began a high fat content meal 30 minutes prior to drug administration. Subjects consumed this meal in 30 minutes or less; however, the study drug was administered 30 minutes after the start of the meal. The FDA standard high-fat content breakfast consisted of the following: 2 eggs fried in butter, 2 strips of bacon, 2 slices of toast with butter, 4 ounces of hash brown potatoes and 8 fluid ounces (.about.240 mL) of whole milk.

No food was allowed for at least 4 hours post-dose. At 4.5, 9.5, and 13.5 hours post-dose, standardized meals and beverages were provided to the subjects. All meals and beverages were free of alcohol, grapefruit products, xanthines and caffeine and were identical for both study treatments.

Treatments Administered

Following an overnight fast of at least 10 hours, and 30 minutes after the start of a high fat content meal, subjects received one of the following treatments at 0.00 hour on Day 1 of the study period according to a randomization scheme:

Treatment A: 2 triple combination capsules (dry formulation) with 240 mL of ambient temperature water (Treatment Dose=190 mg of clarithromycin, 90 mg of rifabutin and 20 mg of clofazimine).

Treatment B: 2 triple combination capsules (PEG formulation) with 240 mL of ambient temperature water (Treatment Dose=190 mg of clarithromycin, 90 mg of rifabutin and 20 mg of clofazimine).

The medications were administered orally. The drugs were given 1 or more capsules at a time. All capsules were ingested within 1 minute.

Blood Processing

Approximately 236.5 mL, of blood was collected from male subjects and 241.5 mL of blood was collected from female subjects over the study period, as detailed in:

TABLE 1

| Procedure | Volume Taken per Subject | |
| --- | --- | --- |
| | Male Subjects | Female Subjects |
| Pre-Study | 19.5 mL | 19.5 mL |
| Serum p-CG Tests | N/AP | 5 mL |
| Interim Lab Tests (Biochemistry and Haematology) | 13.5 mL | 13.5 mL |
| PK Blood Samples | 190 mL | 190 mL |
| End-of-Study Examination | 13.5 mL | 13.5 mL |
| Total Blood Volume | 236.5 mL | 241.5 mL |

During the study period, 19 blood samples (1.times.4 mL and 1.times.6 mL tube for each sampling time point) were collected from each subject by direct venipuncture or by Vasofix® intravenous catheter using pre-cooled, labelled blood collection tubes containing potassium ethylenediaminetetraacetic acid (EDTA) as the anticoagulant. Blood samples were collected at 0.00 (pre-dose), 0.25, 0.50, 0.75, 1.00, 1.50, 2.00, 2.50, 3.00, 4.00, 6.00, 8.00, 10.00, 12.00, 16.00, 24.00, 48.00, 60.00, and 96.00 hours post-dose. The clock times of all blood draws for plasma concentration analyses were recorded.

The 6 mL tubes were used to measure clarithromycin and 14-hydroxyclarithromycin. The 4 mL tubes were used to measure rifabutin, 25-O-desacetylrifabutin and clofazimine.

The blood samples were stored in an ice bath before centrifugation and were centrifuged as soon as possible under refrigerated conditions (at 4° C.) at 3500 rpm for 7 minutes. The collected plasma from each blood collection tube was aliquotted into pre-cooled labelled polypropylene tubes. A minimum of 1.5 mL of plasma was transferred from the 6 mL tubes into the first polypropylene tube, and all remaining plasma, if any, was transferred into a second polypropylene tube. The samples were kept in an ice bath, and flash frozen in an upright position, then stored at −70±10° C. until assayed.

In another procedure, the blood samples were stored in an ice bath before centrifugation and were centrifuged as soon as possible under refrigerated conditions (at 4° C.) at 3500 rpm for 7 minutes. The collected plasma from each blood collection tube was aliquotted into pre-cooled labelled polypropylene tubes. A minimum of 0.8 mL of plasma was transferred from the 4 mL, tubes into the first polypropylene tube, and all remaining plasma, if any, was transferred into a second polypropylene tube. The samples were kept in an ice bath, and flash frozen in an upright position, then stored at −70±10° C. until assayed.

Upon completion of the clinical portion of the study, all samples were analysed for clarithromycin and 14-hydroxyclarithromycin in the plasma samples or for rifabutin, 25-O-desacetylrifabutin and clofazimine in the plasma samples.

Measurements

The direct measurements of this study were the plasma concentrations of clarithromycin and 4-hydroxyclarithromycin performed, and rifabutin, 25-O-desacetylrifabutin, and clofazimine performed.

The pharmacokinetic parameters were derived from the plasma clarithromycin, 14-hydroxyclarithromycin, rifabutin, 25-O-desacetylrifabutin, and clofazimine concentrations.

Bioanalyses

Clarithromycin and 14-hydroxyclarithromycin—Information about these analytes was obtained using routine methods known in the art.

Rifabutin, 25-O-Desacetylrifabutin, and Clofazimine-Rifabutin, 25-O-desacetylrifabutin, clofazimine, and the internal standard, diltiazem, were extracted by solid phase extraction into an organic medium from 0.20 mL of human plasma. An aliquot of this extract was injected into a High Performance Liquid Chromatography system and detected using a mass spectrometer. The analytes were separated by reverse phase chromatography. Evaluation of the assay was carried out by the construction of an eight (8) point calibration curve (excluding zero concentration) covering the range of 9.996 ng/mL to 1279.470 ng/mL for rifabutin, 2.499 ng/mL to 319.917 ng/mL for 25-O-desacetylrifabutin, and 4.997 ng/mL to 639.586 ng/L., for clofazimine in human plasma.

The slope and intercept of the calibration curves were determined through weighted linear regression analysis (l/conc.$^2$). Two calibration curves and duplicate QC samples (at 3 concentration levels) were analysed along with each batch of the study samples. Peak area ratios were used to determine the concentration of the standards, quality control samples, and the unknown study samples from the calibration curves.

Pharmacokinetic Analysis

The following pharmacokinetic parameters for clarithromycin, rifabutin and clofazimine and the metabolites 14-hydroxyclarithromycin and 25-O-desacetylrifabutin were calculated by standard non-compartmental methods: $AUC_{0-t}$, $AUC_{0-inf}$, $AUC_{0-t}/AUC_{0-inf}$, $C_{max}$, $T_{max}$, $t_{1/2}$, $K_{el}$, and M/P ratio.

Using General Linear Model (GLM) procedures in Statistical Analysis System (SAS), analysis of variance (ANOVA) was performed on ln-transformed $AUC_{0-4}$, $AUC_{0-inf}$, $AUC_{0-t}/AUC_{0-inf}$ and $C_{max}$ and on untransformed $t_{1/2}$ $K_{el}$, and M/P ratio at the significance level of 0.05. The intra-subject coefficient of variation (CV) was calculated using the Mean Square Error (MSE) from the ANOVA table. The ratio of geometric means and the 90% geometric confidence interval (90% C.I.) were calculated based on the difference in the Least Squares Means of the ln-transformed $AUC_{0-t}$, $AUC_{0-inf}$, $AUC_{0-t}/AUC_{0-inf}$ and $C_{max}$ between the dry and PEG formulations. $T_{max}$ was analysed using non-parametric methods.

The pharmacokinetic parameters for clarithromycin, 14-hydroxyclarithromycin, rifabutin, 25-O-desacetylrifabutin, and clofazimine derived for both treatments were:

Primary Parameters:

$AUC_{0-t}$=area under the concentration-time curve from time zero to time of last measurable concentration, calculated using the linear trapezoidal rule $AUC_{0-inf}$=area under the concentration-time curve from time zero to infinity $C_{max}$=maximum plasma concentration after dosing Secondary Parameters:

$AUC_{0-t}/AUC_{0-inf}$=Ratio of $AUC_{0-t}$ to $AUC_{0-inf}$ $T_{max}$=time to reach peak plasma concentration $K_{el}$=first order terminal elimination rate constant $t_{1/2}$=terminal half-life M/P ratio=Metabolite/Parent ratio for $AUC_{0-inf}$ (the conversion to molar units occurs prior to the computation of the ratio).

The arithmetic mean, standard deviation (SD) and CV were calculated for plasma clarithromycin, 14-hydroxyclarithromycin, rifabutin, 25-O-desacetylrifabutin, and clofazimine concentrations for each sampling time and formulation, and for the PK parameters $AUC_{0-t}$, $AUC_{0-inf}$, $AUC_{0-t}/AUC_{0-inf}$, $C_{max}$, $T_{max}$, $t_{1/2}$, $K_{el}$, and M/P ratio.

ANOVAs (with the following factors: treatment, period, sequence, subject within sequence) were performed on the In-transformed data for $AUC_{0-t}$, $AUC_{0-inf}$, $AUC_{0-t}/AUC_{0-inf}$, $C_{max}$. ANOVAs were also performed on the untransformed data to compare the $t_{1/2}$, $K_{el}$, and M/P ratio. All ANOVAs were performed with the SAS GLM Procedure. $T_{max}$ was analysed using nonparametric methods. The equality of treatment effect in both arms was evaluated using Wilcoxon rank-sum tests. For all analyses, effects were considered statistically significant if the p-value associated with was less than or equal to 0.050.

Based on the ANOVA results and the pair-wise comparisons of the In-transformed $AUC_{0-t}$, $AUC_{0-inf}$, $AUC_{0-t}/AUC_{0-inf}$, $C_{max}$ data, the intra-subject CV, the relative ratios of the geometric means (calculated according to the formula: $e^{[dry-PEG]} \times 100\%$), and the 90% geometric C.I. were determined.

Twenty-four subjects participated in this study, and samples from the 24 completing subjects (12 per arm) were assayed for drug concentration.

The principal statistical software used was SAS®, version 8.2. All analyses were performed on the platform of the SAS® suite of statistical programs, using coded procedures that have been written and verified by the staff in the Pharmacokinetics and Statistics Department of BCR.

Twenty-four subjects (12 males and 12 females) with a mean age of 31 years (range=18 to 45 years) were enrolled in and completed the study. The completing subjects' mean height was 170 cm (range=149 to 187 cm) and their mean weight was 71 kg (range=48 to 104 kg). The subjects' mean BMI was 24.7 kg/m² (range=18.6 to 29.7 kg/m2). The completing subjects consisted of 9 Caucasians, 5 Asians, 5 Blacks and 4 Hispanics and 1 Mulatto.

Bioanalytical Results

Clarithromycin and 14-Hydroxyclarithromycin—Information about these analytes was obtained using routine methods known in the art.

Rifabutin, 25-O-Desacetylrifabutin, and Clofazimine—The plasma samples were analysed for rifabutin, 25-O-desacetylrifabutin, and clofazimine.

Accuracy and precision of this method were evaluated both within run (intra-assay—Table 2) and between runs (inter-assay—Table 3) by the analysis of the lowest limit of quantification (LLOQ) and Quality Control samples at 3 different concentrations (QC HIGH, QC MED and QC LOW) in human plasma prepared in the range of the calibration/standard curve. The accuracy and precision determined, at each concentration level, were reported as percent relative error (% RE) and percent coefficient of variation (% CV), respectively.

TABLE 2

Intra-Batch

| | Analyte name | | |
|---|---|---|---|
| | Parent rifabutin | Metabolite 25-0-desacetylrifabutin | Parent clofazimine |
| QC Intraday precision range (%) | 4.2 to 8.7 | 5.3 to 10.0 | 2.3 to 7.7 |
| QC Intraday accuracy range (%) | −3.9 to 1.1 | −7.5 to 9.3 | 0.6 to 7.0 |

TABLE 3

Inter-Batch

| | Analyte name | | |
|---|---|---|---|
| | Parent rifabutin | Metabolite 25-0-desacetylrifabutin | Parent clofazimine |
| QC Intraday precision range (%) | 5.1 to 7.6 | 4.9 to 10.4 | 5.1 to 7.2 |
| QC Intraday accuracy range (%) | −0.2 to 3.0 | −1.4 to 3.9 | 0.4 to 5.2 |

Long Term Stability in Matrix—Long term stability of rifabutin, 25-O-desacetylrifabutin, and clofazimine in human plasma can be determined by comparing the concentration of freshly prepared (not frozen) QC samples (QC LOW and QC HIGH) with aged QC samples of the same concentration.

Pharmacokinetic Profiles

Figure 1B:
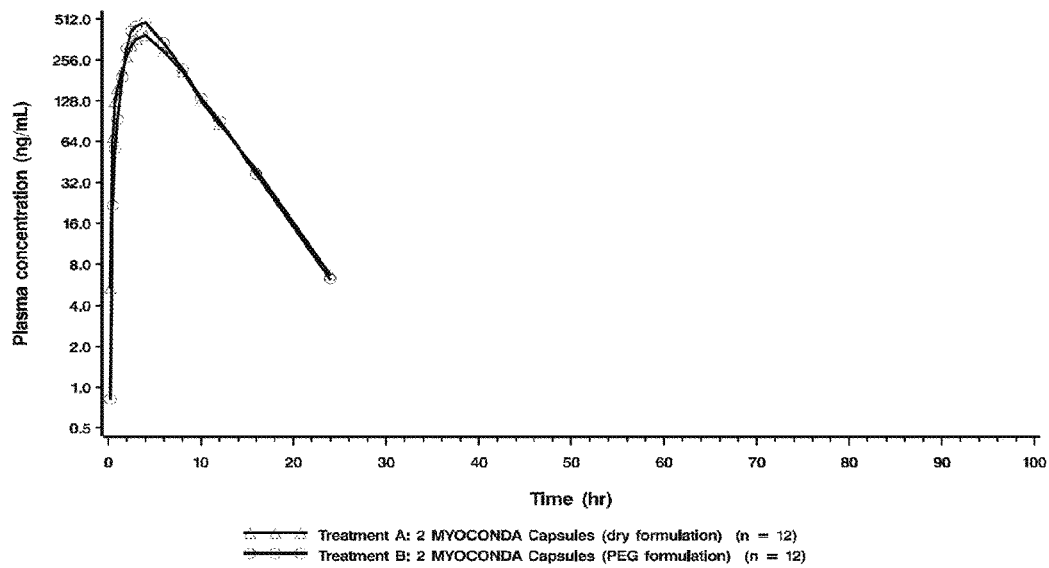
Figure 2A:
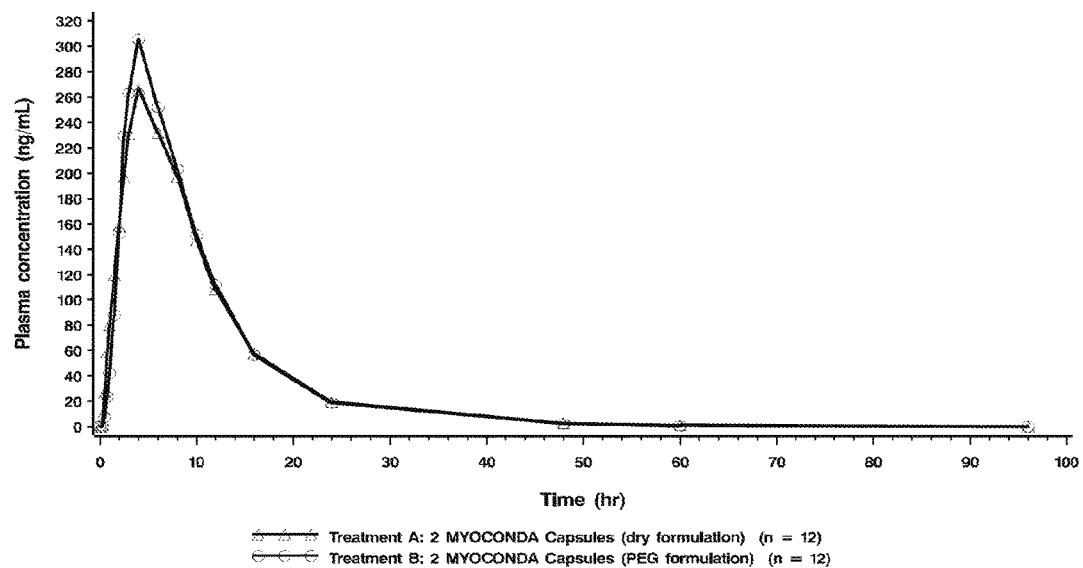
FIGS. 2*a-b* depict mean 14-hydroxyclarithromycin plasma concentration-time profiles in linear and semi-logarithmic plots, respectively.
Figure 2B:
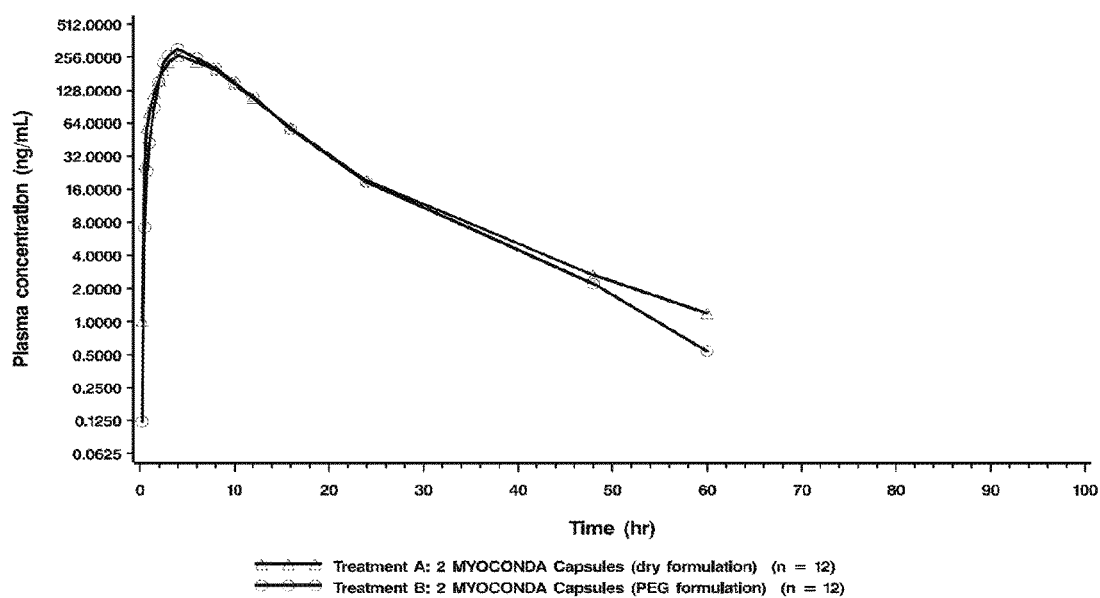
Figure 3A:
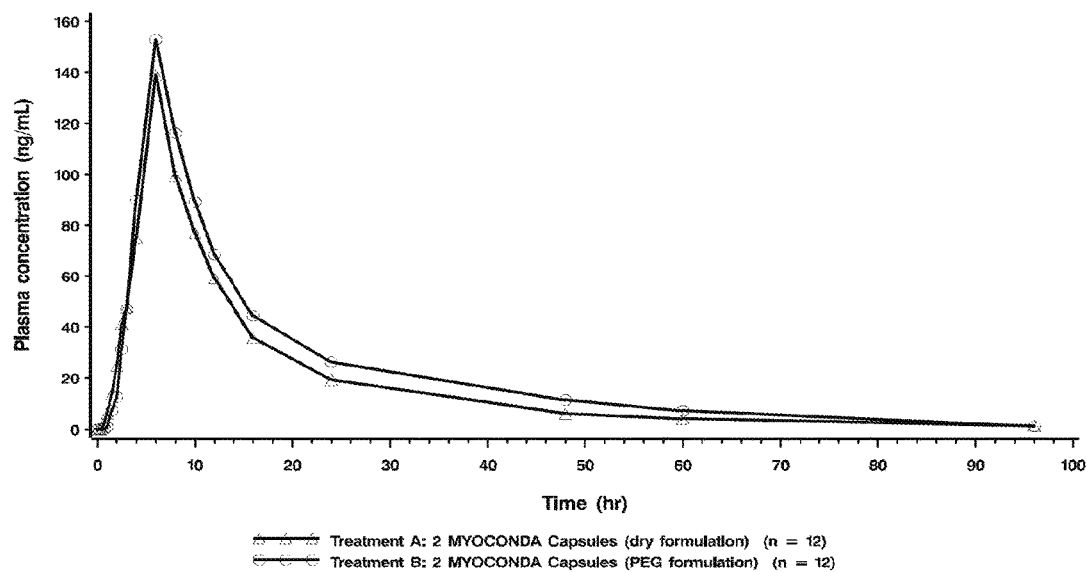
FIGS. 3*a-b* depict mean rifabutin plasma concentration-time profiles in linear and semi-logarithmic plots, respectively.
Figure 3B:
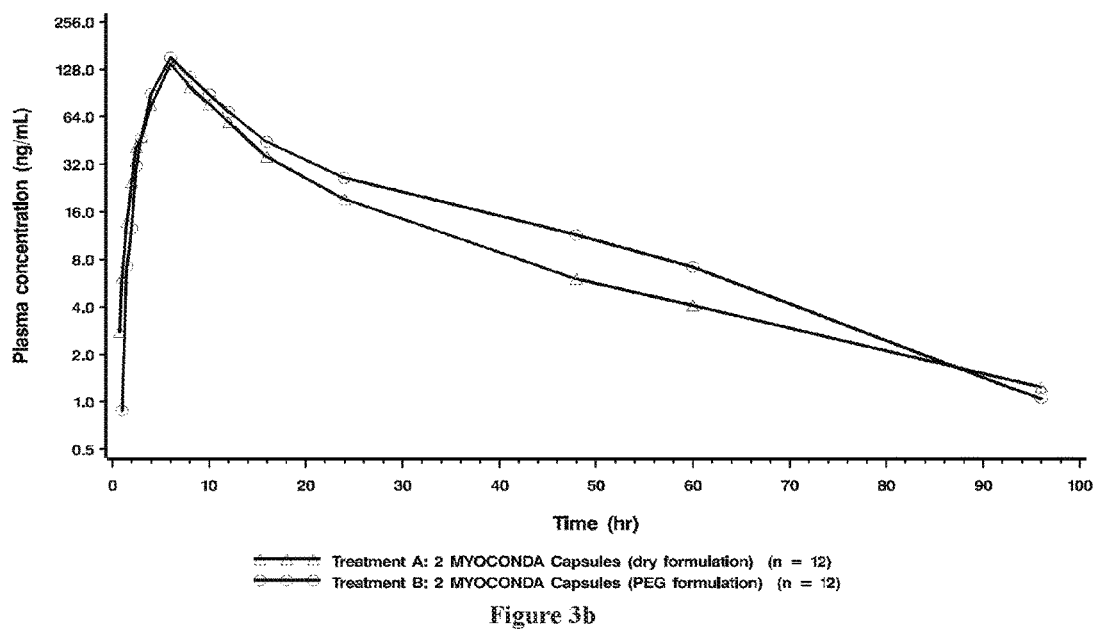
Figure 4A:
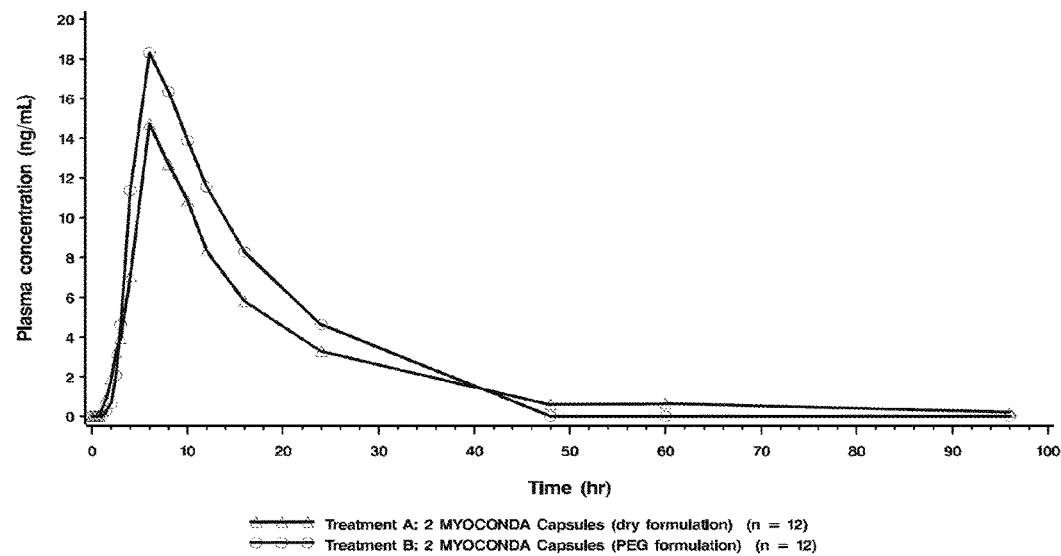
FIGS. 4*a-b* depict mean 25-O-desacetylrifabutin plasma concentration-time profiles in linear and semi-logarithmic plots, respectively.
Figure 4B:
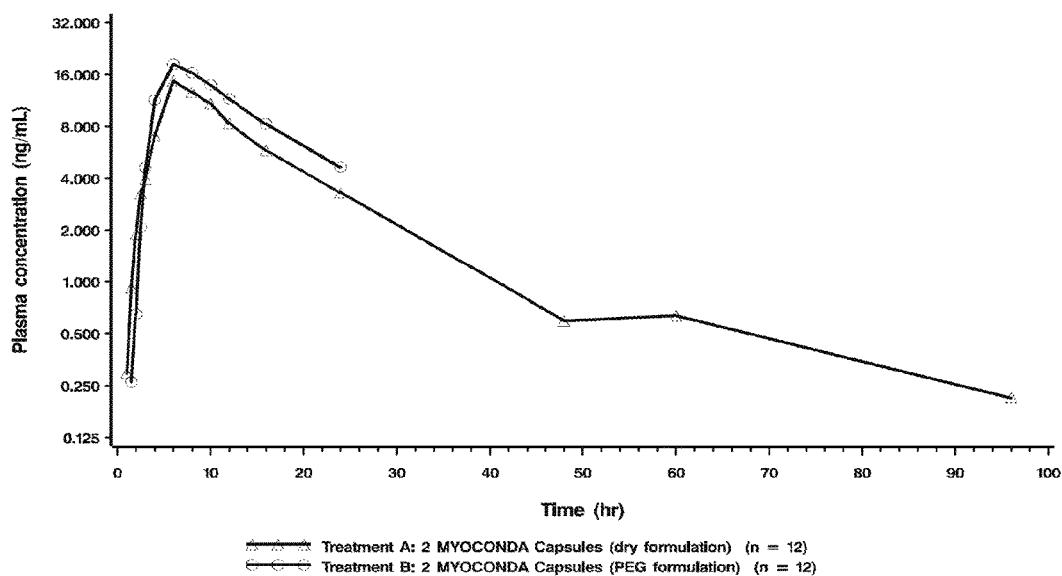
Figure 5A:
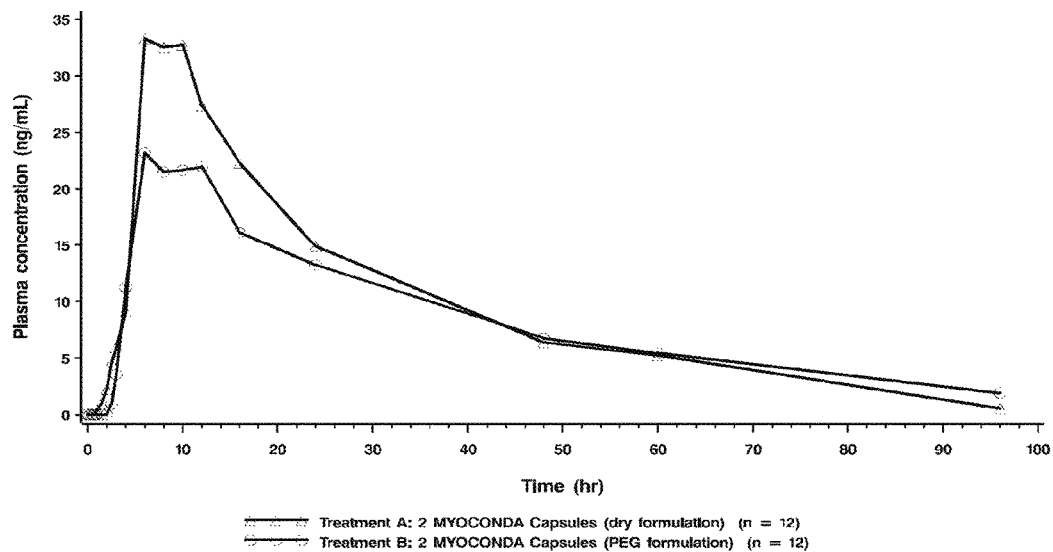
FIGS. 5*a-b* depict mean clofazimine plasma concentration-time profiles in linear and semi-logarithmic plots, respectively.
Figure 5B:
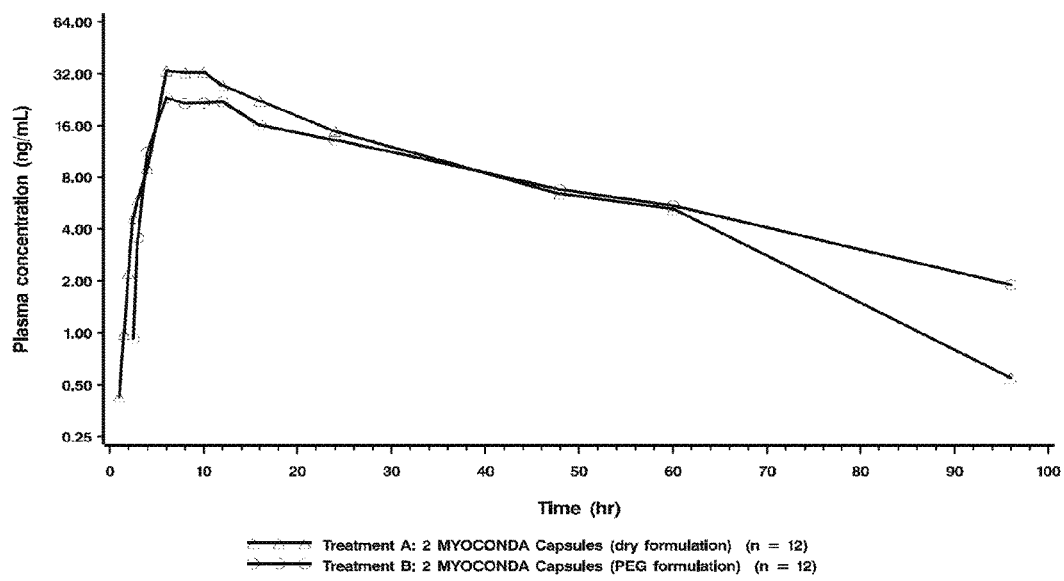

Mean clarithromycin, 14-hydroxyclarithromycin, rifabutin, 25-O-desacetylrifabutin, and clofazimine plasma concentration-time profiles (linear and semi-logarithmic plots) are presented in FIGS. 1, 2, 3, 4, and 5, respectively.

The mean pharmacokinetic parameters for clarithromycin, 14-hydroxyclarithromycin, rifabutin, 25-O-desacetylrifabutin, and clofazimine are summarized below in Tables 4, 5, 6, 7, and 8, respectively.

TABLE 4

PHARMACOKINETIC PARAMETERS FOR CLARITHROMYCIN

| | Geometric Mean (% CV) Arithmetic Mean ± SD | |
|---|---|---|
| Pharmacokinetic Parameters | Triple Combination Capsules (dry formulation) (A) (n = 12) | Triple Combination Capsules (PEG formulation) (B) (n = 12) |
| $AUC_{0-t}$ (ng hr/mL) | 2388.54 (66.38) | 2972.86 (54.97) |
| | 3123.93 ± 2073.75 | 3450.66 ± 1896.84 |
| $AUC_{0-inf}$ (ng hr/mL) | 2462.93 (65.56) | 3049.00 (54.50) |
| | 3194.76 ± 2094.48 | 3520.31 ± 1918.52 |
| $AUC_{0-t}/AUC_{0-inf}$ (%) | 96.98 (1.76) | 97.50 (1.96) |
| | 96.99 ± 1.70 | 97.52 ± 1.91 |
| $C_{max}$ (ng/mL) | 364.30 (55.76) | 485.54 (46.14) |
| | 450.69 ± 251.30 | 549.18 ± 253.41 |
| $T_{max}$ (hr)* | 4.00 (1.00-6.00) | 4.00 (2.00-6.00) |
| $T_{1/2}$ (hr) | 3.13 ± 0.72 | 3.17 ± 0.52 |
| $K_{el}$ (hr$^{-1}$) | 2.35E-01 ± 6.74E-02 | 2.24E-01 ± 3.75E-02 |

TABLE 5

PHARMACOKINETIC PARAMETERS FOR 14-HYDROXYCLARITHROMYCIN

| | Geometric Mean (% CV) Arithmetic Mean ± SD | |
|---|---|---|
| Pharmacokinetic Parameters | Triple Combination Capsules (dry formulation) (A) (n = 12) | Triple Combination Capsules (PEG formulation) (B) (n = 12) |
| $AUC_{0-t}$ (ng hr/mL) | 2671.07 (49.71) | 2868.16 (34.51) |
| | 3015.37 ± 1499.06 | 3119.41 ± 1076.45 |
| $AUC_{0-inf}$ (ng hr/mL) | 2704.76 (49.93) | 2904.20 (33.94) |
| | 3055.45 ± 1525.66 | 3145.08 ± 1067.45 |

TABLE 5-continued

PHARMACOKINETIC PARAMETERS FOR 14-HYDROXYCLARITHROMYCIN

| | Geometric Mean (% CV) Arithmetic Mean ± SD | |
|---|---|---|
| Pharmacokinetic Parameters | Triple Combination Capsules (dry formulation) (A) (n = 12) | Triple Combination Capsules (PEG formulation) (B) (n = 12) |
| $AUC_{0-t}/AUC_{0-inf}$ (%) | 98.75 (1.05) 98.76 ± 1.03 | 98.76 (1.61) 98.77 ± 1.59 |
| $C_{max}$ (ng/mL) | 261.17 (48.85) 292.43 ± 142.86 | 296.82 (34.49) 324.26 ± 111.82 |
| $T_{max}$ (hr)* | 4.00 (2.00-8.00) | 4.00 (2.50-6.00) |
| $T_{1/2}$ (hr) | 7.52 ± 2.44 | 6.66 ± 1.82 |
| $K_{el}$ (hr$^{-1}$) | 1.04E-01 ± 4.21E-02 | 1.12E-01 ± 3.14E-02 |
| M/P Ratio (hr) | 1.20 ± 0.63 | 0.99 ± 0.37 |

TABLE 6

PHARMACOKINETIC PARAMETERS FOR RIFABUTIN

| | Geometric Mean (% CV) Arithmetic Mean ± SD | |
|---|---|---|
| Pharmacokinetic Parameters | Triple Combination Capsules (dry formulation) (A) (n = 12) | Triple Combination Capsules (PEG formulation) (B) (n = 12) |
| $AUC_{0-t}$ (ng hr/mL) | 1461.26 (57.71) 1633.40 ± 942.60 | 1897.71 (36.42) 2023.01 ± 736.79 |
| $AUC_{0-inf}$ (ng hr/mL) | 1499.70 (31.80) 1577.68 ± 501.76† | 2047.97 (39.63) 2200.58 ± 872.14‡ |
| $AUC_{0-t}/AUC_{0-inf}$ (%) | 83.65 (6.71) 83.84 ± 5.63 | 81.83 (8.94) 82.14 ± 7.34 |
| $C_{max}$ (ng/mL) | 142.75 (39.94) 151.41 ± 60.47 | 160.87 (26.66) 166.39 ± 44.37 |
| $T_{max}$ (hr)* | 6.00 (2.50-6.12) | 6.00 (4.00-8.00) |
| $T_{1/2}$ (hr) | 10.80 ± 5.68† | 14.43 ± 6.83‡ |
| $K_{el}$ (hr$^{-1}$) | 8.44E-02 ± 4.77E-02† | 6.07E-02 ± 3.30E-02‡ |

TABLE 7

PHARMACOKINETIC PARAMETERS FOR 25-0-DESACETYLRIFABUTIN

| | Geometric Mean (% CV) Arithmetic Mean ± SD | |
|---|---|---|
| Pharmacokinetic Parameters | Triple Combination Capsules (dry formulation) (A) (n = 12) | Triple Combination Capsules (PEG formulation) (B) (n = 12) |
| $AUC_{0-t}$ (ng hr/mL) | 1461.26 (57.71) 1633.40 ± 942.60 | 1897.71 (36.42) 2023.01 ± 736.79 |
| $AUC_{0-inf}$ (ng hr/mL) | 1499.70 (31.80) 1577.68 ± 501.76† | 2047.97 (39.63) 2200.58 ± 872.14‡ |
| $AUC_{0-t}/AUC_{0-inf}$ (%) | 83.65 (6.71) 83.84 ± 5.63 | 81.83 (8.94) 82.14 ± 7.34 |
| $C_{max}$ (ng/mL) | 142.75 (39.94) 151.41 ± 60.47 | 160.87 (26.66) 166.39 ± 44.37 |
| $T_{max}$ (hr)* | 6.00 (2.50-6.12) | 6.00 (4.00-8.00) |
| $T_{1/2}$ (hr) | 10.80 ± 5.68† | 14.43 ± 6.83‡ |
| $K_{el}$ (hr$^{-1}$) | 8.44E-02 ± 4.77E-02† | 6.07E-02 ± 3.30E-02‡ |

TABLE 8

PHARMACOKINETIC PARAMETERS FOR CLOFAZIMINE

| | Geometric Mean (% CV) Arithmetic Mean ± SD | |
|---|---|---|
| Pharmacokinetic Parameters | Triple Combination Capsules (dry formulation) (A) (n = 12) | Triple Combination Capsules (PEG formulation) (B) (n = 12) |
| $AUC_{0-t}$ (ng hr/mL) | 696.93 (57.71) 829.07 ± 461.86 | 680.75 (47.37) 769.72 ± 364.62 |
| $AUC_{0-inf}$ (ng hr/mL) | 1242.28 (37.19) 1304.12 ± 484.95† | 1030.78 (41.69) 1088.58 ± 453.78‡ |
| $AUC_{0-t}/AUC_{0-inf}$ (%) | 76.08 (17.55) 77.55 ± 13.61 | 64.28 (27.44) 68.26 ± 18.73 |
| $C_{max}$ (ng/mL) | 33.01 (54.75) 38.32 ± 20.98 | 27.82 (38.14) 29.82 ± 11.37 |
| $T_{max}$ (hr)* | 8.00 (2.50-24.00) | 8.00 (4.00-12.00) |
| $T_{1/2}$ (hr) | 23.25 ± 4.49† | 21.28 ± 8.27‡ |
| $K_{el}$ (hr$^{-1}$) | 3.07E-02 ± 5.75E-03† | 3.55E-02 ± 1.14E-02‡ |

The relative bioavailability analysis results for $AUC_{0-t}$, $AUC_{0-inf}$, $AUC_{0-t}/AUC_{0-inf}$, $C_{max}$, and for clarithromycin, 14-hydroxyclarithromycin, rifabutin, 25-O-desacetylrifabutin, and clofazimine are summarized above in Tables 9, 10, 11, 12, and 13, respectively.

TABLE 9

RELATIVE BIOAVAILABILITY ASSESSMENTS FOR CLARITHROMYCIN

| Parameter | 90% C.I. | Ratio of Means |
|---|---|---|
| $AUC_{0-t}$ | 47.58% to 135.69% | 80.34% |
| $AUC_{0-inf}$ | 48.33% to 135.03% | 80.78% |
| $C_{max}$ | 46.57% to 120.88% | 75.03% |

TABLE 10

RELATIVE BIOAVAILABILITY ASSESSMENTS FOR 14-HYDROXYCLARITHROMYCIN

| Parameter | 90% C.I. | Ratio of Means |
|---|---|---|
| $AUC_{0-t}$ | 65.11% to 133.20% | 93.13% |
| $AUC_{0-inf}$ | 65.43% to 132.57% | 93.13% |
| $C_{max}$ | 61.72% to 125.43% | 87.99% |

TABLE 11

RELATIVE BIOAVAILABILITY ASSESSMENTS FOR RIFABUTIN

| Parameter | 90% C.I. | Ratio of Means |
|---|---|---|
| $AUC_{0-t}$ | 57.12% to 103.80% | 77.00% |
| $AUC_{0-inf}$ | 53.02% to 101.13% | 73.23% |
| $C_{max}$ | 71.44% to 110.23% | 88.74% |

TABLE 12

RELATIVE BIOAVAILABILITY ASSESSMENTS FOR 25-0-DESACETYLRIFABUTIN

| Parameter | 90% C.I. | Ratio of Means |
|---|---|---|
| $AUC_{0-t}$ | 48.10% to 113.68% | 73.95% |
| $AUC_{0-inf}$ | 56.74% to 130.54% | 86.06% |
| $C_{max}$ | 55.19% to 97.71% | 73.43% |

TABLE 13

RELATIVE BIOAVAILABILITY ASSESSMENTS FOR CLOFAZIMINE

| Parameter | 90% C.I. | Ratio of Means |
|---|---|---|
| $AUC_{0-t}$ | 66.12% to 158.52% | 102.38% |
| $AUC_{0-inf}$ | 75.50% to 192.39% | 120.52% |
| $C_{max}$ | 83.26% to 169.02% | 118.63% |

Pharmacokinetic Conclusions

Based on data from 12 completing subjects per arm, the pharmacokinetics of clarithromycin, 14-hydroxyclarithromycin, rifabutin, 25-O-desacetylrifabutin, and clofazimine data were assessed from the following treatments:

Treatment A: Triple Combination Capsules (dry formulation)

Treatment B: Triple Combination Capsules (PEG formulation)

Pharmacokinetic Analysis of Clarithromycin:

The peak and systemic exposures of clarithromycin were ~25% and ~20% lower after the single oral dose of triple combination capsules (dry formulation) when compared to triple combination capsules (PEG formulation). Also, the statistical results indicated that the 90% confidence intervals of the geometric mean ratios (dry/PEG) for $AUC_{0-t}$, $AUC_{0-inf}$, and $C_{max}$ were 47.58% to 135.69%, 48.33% to 135.03%, and 46.57% to 120.88%, respectively.

A single dose of 250 mg of clarithromycin resulted in a $C_{max}$ of 780±250 ng/mL. The results obtained from dry and PEG formulations of triple combination capsules were approximately proportional to literature findings. Chu et al. (1993) reported that the rise of clarithromycin peak concentrations occur non-linearly to dose which might explain any slight disproportionality between the literature values and those obtained from triple combination capsules dry and PEG formulations.

There was however, no significant difference in the rate of exposure ($T_{max}$) of clarithromycin between the 2 formulations, indicating a similar rate of absorption between the dry and PEG formulations (Median $T_{max}$ 4.00 hours). Similarly, the elimination half-life was also found to be similar between the dry and PEG formulations (p value>0.05).

Pharmacokinetic Analysis of 14-Hydroxyclarithromycin:

The peak and systemic exposures of the metabolite, 14-hydroxyclarithromycin were ~12% and ~7% lower after the single oral dose of triple combination capsules (dry formulation) when compared to triple combination capsules (PEG formulation). Also, the statistical results indicated that the 90% confidence intervals of the geometric mean (dry/PEG) for $AUC_{0-t}$, $AUC_{0-inf}$ and $C_{max}$ were 65.11% to 133.20%, 65.43% to 132.57%, and 61.72% to 125.43%, respectively.

Similar to the parent compound, there was no significant difference in the rate of exposure ($T_{max}$) of 14-hydroxyclarithromycin between the 2 formulations, indicating a similar rate of absorption between the dry and PEG formulations (Median $T_{max}$ 4.00 hours). Similarly, the elimination half-life was also found to be similar between the dry and PEG formulations (p values>0.05).

Pharmacokinetic Analysis of Rifabutin:

The peak and systemic exposures of rifabutin were ~11% and ~23% lower after the single oral dose of triple combination capsules (dry formulation) when compared to triple combination capsules (PEG formulation). Also, the statistical results indicated that the 90% confidence intervals of the geometric mean ratios (dry/PEG) for $AUC_{0-t}$, $AUC_{0-inf}$ and $C_{max}$ were 57.12% to 103.80%, 53.02% to 101.13%, and 71.44% to 110.23%, respectively.

Gatti et al. (1998) conducted a comparative study of rifabutin absorption and disposition in HIV-infected patients with or without wasting syndrome. They found that the $C_{max}$ (peak concentration) was 340±140 ng/ml, in 10 HIV patients without wasting syndrome after a single 300 mg dose of rifabutin administered under fasting conditions.

There was however, no significant difference in the rate of exposure ($T_{max}$) of rifabutin between the 2 formulations, indicating a similar rate of absorption between the dry and PEG formulations (Median $T_{max}$ 6.00 hours). Similarly, the elimination half-life was also found to be similar between the dry and PEG formulations (p values>0.05).

Pharmacokinetic Analysis of 25-O-Desacetylrifabutin:

The peak and systemic exposures of the metabolite 25-O-desacetylrifabutin were ~26% lower after the single oral dose of triple combination capsules (dry formulation) when compared to triple combination capsules (PEG formulation). Also, the statistical results indicated that the 90% confidence intervals of the geometric mean ratios (dry/PEG) for $AUC_{0-t}$ and $C_{max}$ were 55.19% and 97.71%, respectively. Approximately 65% of subjects were excluded from the statistical analysis of $AUC_{0-inf}$, $K_{el}$, and $t_{1/2}$ due to the $AUC_{0-inf}$ extrapolation being more than 20%. Hence, the pharmacokinetic discussion was not based on the outcome of $AUC_{0}$-inf.

Similar to the parent compound, there was no significant difference in the rate of exposure ($T_{max}$) of 25-O-desacetylrifabutin between the 2 formulations, indicating a similar rate of absorption between the dry and the PEG formulation (Median dry and PEG $T_{max}$ 6.01 hours and 7.04 hours, respectively). Similarly, the elimination half-life was also found to be similar between the dry and PEG formulations (p values>0.05).

Pharmacokinetic Analysis of Clofazimine:

The peak exposure of clofazimine was ~19% ($C_{max}$) higher after the single oral dose of triple combination capsules (dry formulation) when compared to triple combination capsules (PEG formulation). However, the total systemic exposure ($AUC_{0-t}$) was found to be similar between the 2 formulations, with a geometric mean ratio of 102%. The statistical results indicated that the 90% confidence intervals of the geometric mean ratios (dry/PEG) for $AUC_{0-t}$ and $C_{max}$ were 66.12% to 158.52%, and 83.26% to 169.02%, respectively. Approximately 50% (Treatment A) and 75% (Treatment B) of subjects were excluded from the statistical analysis of $AUC_{0-inf}$, $K_{el}$ and $t_{1/2}$ due to the $AUC_{0-inf}$ extrapolation being more than 20%. Hence, the pharmacokinetic discussion was not based on the outcome of $AUC_{0-inf}$.

Nix et al. (2004) reported proportional values after administration of a 200 mg dose. The $C_{max}$ was found to be 227 ng/mL. These values are proportional to the values obtained from administration of triple combination capsules in the current study.

There was however, no significant difference in the rate of exposure (T) of clofazimine between the 2 formulations, indicating a similar rate of absorption between the dry and PEG formulations (Median T.sub.max 8.00 hours). Similarly, the elimination half-life was also found to be similar between the dry and PEG formulations (p values>0.05).

Conclusion

The relative bioavailability of clarithromycin, rifabutin, clofazimine, and their metabolites were assessed by measuring and comparing the peak and total systemic exposures from the 2 treatments (using $AUC_{0-t}$, $AUC_{0-inf}$ and $C_{max}$).

The dry/PEG geometric mean ratios of the total systemic exposures (AUCs) for clarithromycin, rifabutin and their metabolites were lower by ~7%-26%. Similarly, the dry/PEG geometric mean ratios of the peak systemic exposures ($C_{max}$) for clarithromycin, rifabutin, and their metabolites were found to be ~11%-26% lower when compared to the PEG formulation. However, the total systemic exposures for clofazimine ($AUC_{0-t}$) were similar between the dry formulation and the PEG formulation. The peak exposure of the dry formulation was ~19% ($C_{max}$) higher than that of the PEG formulation. There was no significant difference in the time to peak concentration for any of the analytes from either the dry or the PEG formulation treatment group.

Overall, triple combination (dry and PEG formulations) were well tolerated as a single-dose of about 190 mg of clarithromycin, about 90 mg of rifabutin, and about 20 mg of clofazimine, and no significant safety issues emerged.

2 $C_{max}$ Comparisons with Literature Values

Clofazimine—$C_{max}$ fed=227 ng/ml after 200 mg dose (Nix, et al., 2004).

Triple combination (dry form) 38.32±20.98 ng/mL. Triple combination (PEG form). 29.82±11.37 ng/mL (Bioavailability study with 20 mg). 20 mg dose gives $C_{max}$ of 23 ng/mL.

Rifabutin—$C_{max}$ (peak concentration) was 340±140 ng/mL in 10 HIV patients without wasting syndrome after a single 300-mg dose of rifabutin administered fasting (Comparative study of rifabutin absorption and disposition in HIV-infected patients with or without wasting syndrome. Gatti G, Di Biagio A, De Pascalis C, Guerra M, Bassetti M, Bassetti D. Int Conf AIDS. 1998; 12: 554 (abstract no. 32171)).

Triple combination (dry form) 151.41±60.47 ng/mL. Triple combination (PEG Form) 166.39±44.37 ng/mL (Bioavailability study with 90 mg). 90 mg dose gives $C_{max}$ of 102 ng/mL.

Clarithromycin—500 mg (four 125-mg capsules, Abbott Laboratories) every 12 hours for 5 doses. $C_{max}$ 2410±670 mg/L and 660±210 ng/mL for metabolite. Single dose of 250 mg resulted in $C_{max}$ of 780±250 ng/mL.

Triple combination (dry form) 450.69±251.30, Triple Combination (PEG Form) 549.18±253.41 (Bioavailability study with 190 mg). 190 mg dose gives $C_{max}$ of 593 ng/mL.

Equivalents

Those skilled in the art will recognize, or be able to ascertain using no more than routine experimentation, numerous equivalents to the compounds, compositions, and methods of use thereof described herein. Such equivalents are considered to be within the scope of the present disclosure and are covered by the following embodiments.

The contents of all references, patents and published patent applications cited throughout this Application, as well as their associated figures are hereby incorporated by reference in their entirety.

It will be appreciated by persons skilled in the art that numerous variations and/or modifications may be made to the invention as shown in the specific embodiments without departing from the scope of the invention as broadly described. The present embodiments are, therefore, to be considered in all respects as illustrative and not restrictive.

What is claimed is:

1. A method of treating a patient infected with a *Mycobacterium avium* complex pathogen comprising: administering a pharmaceutical composition to a patient in need thereof, wherein the pharmaceutical composition comprises a fixed-dose combination of rifabutin, clarithromycin, and clofazimine-polymer solid dispersion, wherein the co-formulated fixed-dose combination comprises 30-60 mg rifabutin, 65-125 mg clarithromycin-and 4-16 mg clofazimine.

2. The method of claim 1, wherein rifabutin is at a dose of 30 mg, clarithromycin is at a dose of 95 mg, and clofazimine is at a dose of 10 mg.

3. The method of claim 1, wherein rifabutin is at a dose of 45 mg, clarithromycin is at a dose of 95 mg, and clofazimine is at a dose of 10 mg.

4. The method of claim 1, wherein the pharmaceutical composition is a tablet.

5. The method of claim 1, wherein the pharmaceutical composition is a capsule.

6. The method of claim 1, wherein the patient is in need of treatment for an infection with *M. avium*.

7. The method of claim 1, wherein the patient is in need of treatment for an infection with *M. avium* subsp. *paratuberculosis*.

8. A method of treating a patient with *Mycobacterium avium* subsp. *paratuberculosis* comprising: administering a pharmaceutical composition to a patient in need thereof, wherein the pharmaceutical composition comprises a fixed-dose combination of rifabutin, clarithromycin, and clofazimine-polymer solid dispersion, wherein the co-formulated fixed-dose combination comprises 30-60 mg rifabutin, 65-125 mg clarithromycin-and 4-16 mg clofazimine.

9. The method of claim 8, wherein rifabutin is at a dose of 45 mg, clarithromycin is at a dose of 95 mg, and clofazimine is at a dose of 10 mg.

10. The method of claim 8, wherein the pharmaceutical composition is a capsule.

11. The method of claim 8, wherein the patient is in need of treatment for Crohn's disease.

* * * * *